United States Patent [19]
Dow

[11] Patent Number: 5,908,930
[45] Date of Patent: Jun. 1, 1999

[54] 5,10-DIHYDROPYRIMDO[4,5-B]QUINOLIN-4 (1H)-ONE TYROSINE KINASE INHIBITORS

[75] Inventor: Robert L. Dow, Waterford, Conn.

[73] Assignee: Pfizer Inc., New York, N.Y.

[21] Appl. No.: 08/894,587

[22] PCT Filed: Mar. 15, 1995

[86] PCT No.: PCT/IB95/00172

§ 371 Date: Aug. 22, 1997

§ 102(e) Date: Aug. 22, 1997

[87] PCT Pub. No.: WO96/28444

PCT Pub. Date: Sep. 19, 1996

[51] Int. Cl.$^6$ ...................... C07D 471/04; A61K 31/505; A61K 31/535
[52] U.S. Cl. ........................... 544/115; 544/60; 544/250; 514/228.5; 514/232.5; 514/232.8; 514/267
[58] Field of Search ..................................... 544/250, 115, 544/60; 514/232.5, 232.8, 228.5, 267

[56] References Cited

U.S. PATENT DOCUMENTS 4,277,603  7/1981  Tolman et al. ........................... 544/250

FOREIGN PATENT DOCUMENTS 511792    11/1992  European Pat. Off. .
WO9628444  9/1996  WIPO .

OTHER PUBLICATIONS

E. Campaigne and G. Randau, "An Unusual Arylation of 4–Oxo–3,4–dihydropyrimido[4,5–b]quinoline (1)", Journal of Heterocyclic Chemistry; vol. 8, pp. 111–120, (Feb. 1971).

Dow et al. Bioorganic & Medicinal Chemistry Letters, vol. 5, pp. 1007–1010, May 4, 1995.

Clark et al., J.C.S. Perkin Transactions I, pp. 131–138, 1976.

Burke, Jr., Stem Cells, vol. 12, pp. 1–6, 1994.

*Primary Examiner*—Emily Bernhardt
*Attorney, Agent, or Firm*—Peter C. Richardson; Gregg C. Benson; A. Dean Olson

[57] ABSTRACT

Certain 5,10-dihydropyrimido[4,5-b]quinolin-4(1 H)-one compounds, and their pharmaceutically-acceptable salts, are useful as inhibitors of tyrosine kinase enzymes and for the treatment of tyrosine kinase dependent diseases (e.g., cancer, atherosclerosis, antiangiogenesis).

9 Claims, No Drawings

5,10-DIHYDROPYRIMDO[4,5-B]QUINOLIN-4 (1H)-ONE TYROSINE KINASE INHIBITORS

This application was filed under 35 U.S.C. §371 based on PCT/IB95/00172, which was filed on Mar. 15, 1995.

This invention relates to 5,10-dihydropyrimido-[4,5-b] quinolin-4(1 H)-one compounds which are tyrosine kinase inhibitors, pharmaceutical compositions containing such tyrosine kinase inhibitors, and the use of such tyrosine kinase inhibitors to treat tyrosine kinase dependent diseases such as cancer, antiangiogenesis and atherosclerosis, in mammals.

BACKGROUND OF THE INVENTION

Tyrosine-specific protein kinases (tyrosine kinases) represent a family of enzymes which catalyze the transfer of the terminal phosphate of adenosine triphosphate to tyrosine residues in protein substrates. The first members of this class to be identified were tyrosine kinases associated with viral genes (termed oncogenes) which were capable of cell transformation (i.e. pp60v-src and pp98v-fps). Later it was shown that there were normal cellular counterparts (i.e. pp60c-src and pp98c-fps) to these viral gene products. A third category of tyrosine kinases to be identified are those termed the growth factor receptors, which includes insulin, epidermal growth factors, and p185 HER-2 receptors. All of these tyrosine kinases are believed, by way of substrate phosphorylation, to play critical roles in signal transduction for a number of cell functions.

Though the exact mechanisms of signal transduction have yet to be elucidated, tyrosine kinases have been shown to be important contributing factors in cell proliferation, carcinogenesis and cell differentiation. Therefore, inhibitors of these tyrosine kinases are useful for the prevention and chemotherapy of proliferative diseases dependent on these enzymes.

SUMMARY OF THE INVENTION

This invention is directed to 5,10-dihydropyrimido[4,5-b]quinolin-4(1 H)-one compounds that are useful as tyrosine kinase inhibitors. The compounds of this invention have Formula I

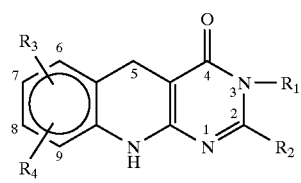

Formula I or their pharmaceutically acceptable salts and prodrugs thereof, wherein $R_1$ is H, alkyl($C_1$–$C_4$), formylalkyl($C_1$–$C_4$), alkyl($C_1$–$C_4$) carbonylalkyl($C_1$–$C_4$), carboxyalkyl($C_1$–$C_4$),alkoxy($C_1$–$C_4$) carbonylalkyl($C_1$–$C_4$), carbamoylalkyl ($C_1$–$C_4$) ,mono-N— or di-N,N-alkyl($C_1$–$C_4$)aminocarbonylalkyl($C_1$–$C_4$), formylcarbamoylalkyl($C_1$–$C_4$), alkanoyl($C_1$–$C_4$) carbamoylalkyl($C_1$–$C_4$), alkoxy($C_1$–$C_4$) carbonylcarbamoylalkyl($C_1$–$C_4$), morpholinocarbonylalkyl ($C_1$–$C_4$), 1-pyrrolidinylcarbonylalkyl($C_1$–$C_4$), 1-piperidinylcarbonylalkyl($C_1$–$C_4$), 4-thiomorpholinylcarbonylalkyl($C_1$–$C_4$), 1-piperazinylcarbonylalkyl($C_1$–$C_4$), 4-alkyl($C_1$–$C_4$)-1-piperazinylcarbonylalkyl($C_1$–$C_4$), hydroxyalkyl($C_1$–$C_4$), alkoxy($C_1$–$C_4$)alkyl($C_1$ –$C_4$), mono-N— or di-N,N-alkyl ($C_1$–$C_4$)aminoalkyl($C_1$–$C_4$), aminoalkyl($C_1$–$C_4$), formylaminoalkyl($C_1$–$C_4$), alkanoyl($C_1$–$C_4$)aminoalkyl ($C_1$–$C_4$), alkoxy($C_1$–$C_4$)carbonylaminoalkyl($C_1$–$C_4$), 1-pyrrolidinylalkyl($C_1$–$C_4$), 1-piperidinylalkyl($C_1$–$C_4$), 4-thiomorpholinylalkyl($C_1$–$C_4$), morpholinoalkyl($C_1$–$C_4$), 1-piperazinylalkyl ($C_1$–$C_4$) or 4-alkyl($C_1$–$C_4$)-1-piperazinylalkyl($C_1$–$C_4$);

$R_2$ is formyl, alkyl($C_1$–$C_4$)carbonyl, carboxy, alkoxy ($C_1$–$C_4$)carbonyl, carbamoyl, mono-N— or di-N,N-alkyl ($C_1$–$C_4$)aminocarbonyl, formylcarbamoyl, alkanoyl($C_1$–$C_4$) carbamoyl, alkoxy($C_1$–$C_4$)carbonylcarbamoyl, morpholinocarbonyl, morpholinoalky($C_1$–$C_4$)carbamoyl, 1-pyrrolidinylcarbonyl, 1-piperidinylcarbonyl, 4-thiomorpholinylcarbonyl, 1-piperazinylcarbonyl or 4-alkyl ($C_1$–$C_4$)-1-piperazinylcarbonyl or such $R_2$ groups substituted on alkyl($C_1$–$C_4$), or $R_2$ is H, alkyl($C_1$–$C_4$), hydroxyalkyl($C_1$–$C_4$), alkoxy($C_1$–$C_4$)alkyl($C_1$–$C_4$), mono-N— or di-N,N-alkyl($C_1$–$C_4$)aminoalkyl($C_1$–$C_4$), aminoalkyl($C_1$–$C_4$), formylaminoalkyl($C_1$–$C_4$), alkanoyl ($C_1$–$C_4$)aminoalkyl($C_1$–$C_4$), alkoxy($C_1$–$C_4$) carbonylaminoalkyl($C_1$–$C_4$), 1-pyrrolidinylalkyl($C_1$–$C_4$), 1-piperidinylalkyl($C_1$–$C_4$), 4-thiomorpholinylalkyl($C_1$–$C_4$), morpholinoalkyl($C_1$–$C_4$), 1-piperazinylalkyl($C_1$–$C_4$) or 4-alkyl($C_1$–$C_4$)-1-piperazinylalkyl($C_1$–$C_4$); and $R_3$ and $R_4$ are each independently H, alkyl($C_1$–$C_4$), perhaloalkyl($C_1$–$C_4$), methoxyphenylthio, alkoxy($C_1$–$C_6$), perhaloalkoxy($C_1$14 $C_6$), formyl, alkyl($C_1$–$C_4$)carbonyl, carboxy, alkoxy($C_1$–$C_4$)carbonyl, carbamoyl, mono-N— or di-N,N— alkyl($C_1$–$C_4$)aminocarbonyl, formylcarbamoyl, alkanoyl($C_1$–$C_4$)carbamoyl, alkoxy($C_1$–$C_4$) carbonylcarbamoyl, morpholinocarbonyl, 1-pyrrolidinylcarbonyl, 1-piperidinylcarbonyl, 4-thiomorpholinylcarbonyl, 1-piperazinylcarbonyl, 4-alkyl ($C_1$–$C_4$)-1-piperazinylcarbonyl, mono-N— or di-N,N-alkyl ($C_1$–$C_4$)amino, amino, formylamino, alkanoyl($C_1$–$C_4$) amino, alkoxy($C_1$–$C_4$)carbonylamino, 1-pyrrolidinyl, 1-piperidinyl, 4-thiomorpholinyl, morpholino, 1-piperazinyl or 4-alkyl($C_1$–$C_4$)-1-piperazinyl;

with the proviso that $R_1$, $R_2$, $R_3$ and $R_4$ are not all H.

A first group of preferred compounds of Formula I are those compounds wherein $R_1$ is H, methyl or morpholinopropyl;
$R_2$ is H or morpholinopropylcarbamoyl;
$R_3$ is 7-methoxy; and
$R_4$ is 8-methoxy.

A second group of preferred compounds of Formula I are those compounds wherein $R_1$ is H;
$R_2$ is alkyl($C_1$–$C_4$);
$R_3$ is H or 7-methoxy; and
$R_4$ is H or 8-methoxy.

A third group of preferred compounds of Formula I are those compounds wherein $R_1$ and $R_2$ are H; and $R_3$ and $R_4$ are each independently alkoxy($C_1$–$C_4$).

Within this third group of preferred compounds of Formula I is a first group of especially preferred compounds wherein $R_3$ is 7-alkoxy($C_1$–$C_4$) and $R_4$ is 8-alkoxy($C_1$–$C_4$).

Within the third group of preferred compounds of Formula I is a second group of especially preferred compounds wherein $R_3$ and $R_4$ are each independently methoxy.

Particularly preferred compounds within the above second group of especially preferred compounds are compounds wherein $R_3$ is 6-methoxy or 8-methoxy and $R_4$ is 9-methoxy.

A fourth group of preferred compounds of Formula I are those compounds wherein $R_3$ is H; and $R_4$ is alkoxy($C_1$–$C_4$).

3

Within this fourth group of preferred compounds of Formula I is a first group of especially preferred compounds wherein $R_1$ and $R_2$ are H; and $R_4$ is 7-methoxy or 8-methoxy.

A particularly preferred compound of Formula I is a compound wherein $R_1$, $R_2$ and $R_3$ are H; and $R_4$ is 7-((4-methoxyphenyl)thio).

The present invention is also directed to pharmaceutical compositions which comprise a therapeutically effective amount of a compound of Formula I and a pharmaceutically-acceptable carrier.

Yet another aspect of this invention is a method of treating tyrosine kinase dependent diseases which comprises administering to a mammal suffering from a tyrosine kinase dependent disease a tyrosine kinase dependent disease treating amount of a compound of Formula I.

By halo is meant chloro, bromo, iodo, or fluoro.

By alkyl is meant straight chain or branched saturated hydrocarbon.

The expression "pharmaceutically-acceptable salts" refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, meglamine (N-methyl-glucamine), benethamine (N-benzylphenethylamine), piperazine or tromethamine (2-amino-2-hydroxymethyl-1,3-propanediol) and nontoxic anionic salts such as (but not limited to) chloride, bromide, iodide, sulfate, bisulfate, phosphate, acetate, maleate, fumarate, oxalate, lactate, tartrate, citrate, gluconate and 4-toluene-sulfonate.

The expression "prodrug" refers to compounds that are drug precursors, which following administration and absorption, release the drug in vivo via some metabolic process. Exemplary prodrugs upon cleavage release the corresponding free acid, and such hydrolyzable ester residues of the Formula I compounds include but are not limited

4 to substituents wherein the $R_1$, $R_2$, $R_3$, or $R_4$ substituents contain carboxyl in which the free hydrogen is replaced by ($C_1$–$C_4$)alkyl, ($C_2$–$C_7$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N, N-($C_1$–$C_2$)alkylamino ($C_2$–$C_3$)alkyl (such as β-dimethylaminoethyl), carbamoyl-($C_1$–$C_2$)alkyl, N,N-di ($C_1$–$C_2$)alkylcarbamoyl-($C_1$–$C_2$)alkyl and piperidino-, pyrrolidino- or morpholino($C_2$–$C_3$)alkyl. In addition, other exemplary prodrugs are those that upon cleavage release the corresponding free amine. Such hydrolyzable amide or imide residues of the Formula I compounds include, but are not limited to, substituents wherein $R_1$, $R_2$, $R_3$, or $R_4$ substituents contain amines in which the free hydrogen is replaced by a variety of acyl moieties.

As used herein, the expression "reaction-inert solvent" refers to a solvent which does not interact with starting materials, reagents, intermediates or products in a manner which adversely affects the yield of the desired product.

One of ordinary skill will recognize that certain substituents detailed in this invention will be chemically incompatible with one another or with the heteroatoms in the compounds, and will avoid these incompatibilities in selecting compounds of this invention.

Other features and advantages will be apparent from the specification and claims.

DETAILED DESCRIPTION OF THE INVENTION

REACTION SCHEME I

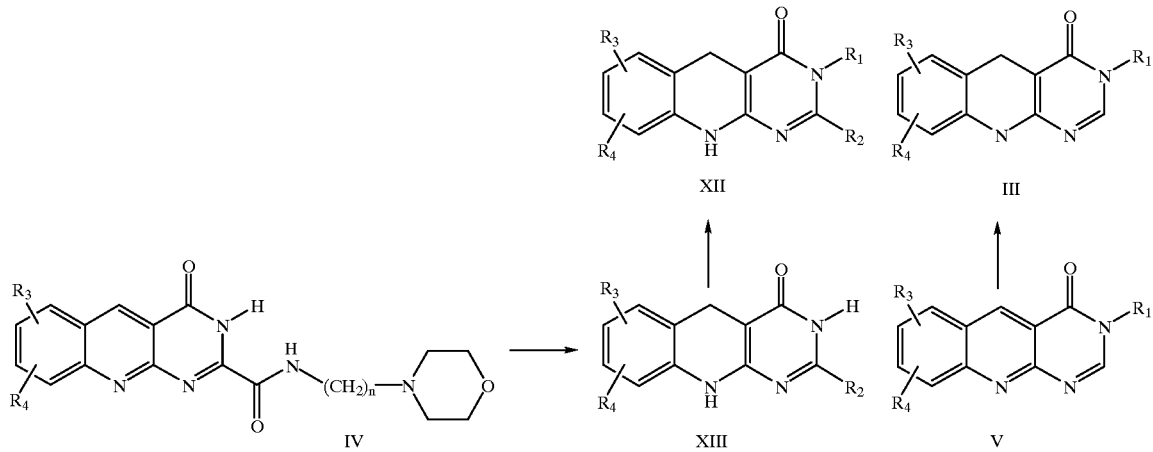

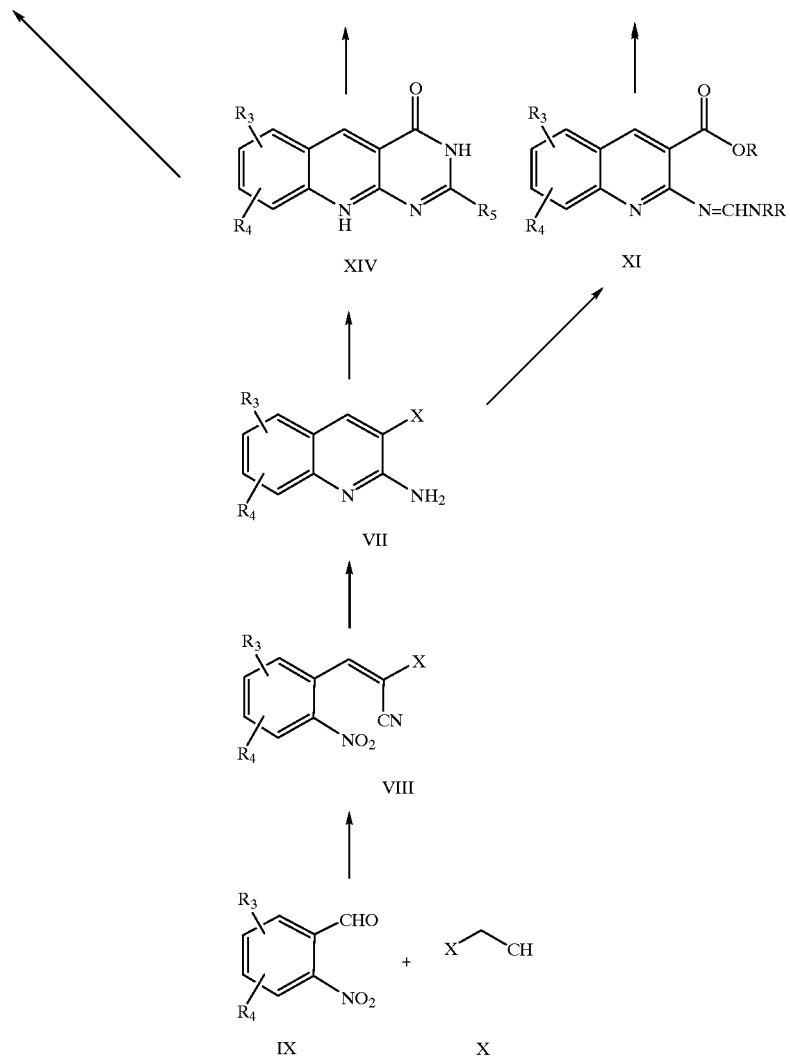

According to Reaction Scheme I the Formula I compounds wherein $R_1$, $R_2$, $R_3$ and $R_4$ are as defined above, with the proviso that $R_1$ is not H (i.e., Formula XII compounds), may be prepared from the appropriate Formula XIII compounds, wherein $R_2$, $R_3$ and $R_4$ are as defined above, by alkylation.

Typically the Formula XIII compounds are heated at 50° C. to 150° C. in a polar solvent such as an aqueous solvent for about 0.5 to 3 hours with the appropriate alkyl halide, sulfonate, or sulfate in the presence of a hydroxide base such as sodium or potassium hydroxide.

The Formula I compounds wherein $R_3$ and $R_4$ are as defined above, with the proviso that when $R_2$ is H, $R_1$ is as defined above and when $R_1$ is H, $R_2$ is as defined above (i.e., Formula III and XIII compounds) may be prepared by reduction of the appropriate Formula IV, V and XIV compounds wherein $R_1$, $R_3$, $R_4$ are as defined above and $R_5$ is as defined for $R_2$ above.

Typically the Formula IV, V and XIV compounds are reduced for example, by hydrogenation (e.g., ammonium formate or hydrogen in the presence of a catalyst), in a polar, high boiling solvent such as formamide, dimethylformamide (DMF) or dimethylsulfoxide (DMSO). The reaction is carried out at elevated temperatures of about 100° C. to 250° C. and pressures of ambient to 100 psi for a period of three to twenty-four hours. Conveniently, pressures of 30 to 100 psi are used for catalytic hydrogenation. Generally an excess of the hydrogen donating species is used and, preferably greater than ten equivalents of the hydrogen donating species is used. Preferably the hydrogen donating species is added portionwise over the course of the reaction when ammonium formate is used.

The Formula IV compounds wherein $R_3$ and $R_4$ are as defined above may be prepared from the appropriate Formula XIV compounds wherein $R_3$ and $R_4$ are as defined above and $R_5$ is an ester that contains a group that is easily displaced (e.g., alkoxy) by condensation with the appropriate amine to produce the desired amide. Generally, the appropriate Formula XIV compound is heated at about 100° C. to 200° C. for about one to three hours in a polar high boiling solvent such as DMSO or DMF with the appropriate amine.

Formula XIV compounds wherein $R_3$ and $R_4$ are as defined above, and $R_5$ is as defined for $R_2$ above (and in addition may be an ester), may be prepared from the appropriate Formula VII compounds, wherein $R_3$ and $R_4$ are as defined above and X is either an ester (that contains an easily displaceable leaving group e.g., alkoxy) or a carbamoyl moiety, by cyclization with an alkyl oxalate compound or a compound of the formula $R_5C(O)NH_2$ or $R_5C(OR)_3$, wherein $R_5$ is as defined above and OR is an easily displaceable leaving group.

Generally the Formula VII compounds are heated neat at 150° C. to 250° C. for about four to twenty-four hours with the appropriate amide or ortho ester. For the case of an orthoester an acid catalyst such as a sulfonic acid or mineral acid is employed.

The Formula VIII compounds wherein $R_3$, $R_4$ and X are as defined above may be prepared by the procedures described in Campaigne, E; Randau, G., *J. Het. Chem.* 1971, 8, 111 and as follows hereinafter.

The Formula VII compounds wherein $R_3$, $R_4$ and X are as defined above may be prepared from the appropriate Formula VIII compounds, wherein $R_3$, $R_4$ and X are as defined above, by reduction. Generally, the Formula VIII compounds are reduced by exposure to a reducing agent (e.g., iron or zinc) in a weak, solubilizing acid such as acetic acid at elevated temperatures of about 50° C. to 150° C.

The Formula VIII compounds wherein $R_3$, $R_4$ and X are as defined above, may be prepared from the appropriate Formula IX compounds wherein $R_3$ and $R_4$ are as defined above by condensation with the appropriate Formula X compound wherein X is as defined above. Typically the Formula IX compounds are reacted with Formula X compounds in the presence of an amine base (e.g., piperidine, pyrrolidine, etc.) in an alcoholic solvent (MeOH, EtOH, etc.) at a temperature of about 50° C. to 100° C. for about two to ten hours.

The Formula V compounds wherein $R_3$, $R_4$ and $R_1$ are as defined above, may be prepared from the appropriate Formula XI compound wherein $R_3$ and $R_4$ are as defined above and N—R—R is an appropriate leaving group (e.g., R is alkyl) by condensation/cyclization with the appropriate amine.

Typically the Formula XI compounds and the appropriate amine are heated at 50° C. to 100° C., preferably at reflux, in a suitable solvent such as an alcohol, a chlorinated solvent, or a polar aprotic solvent for about two hours to eight hours.

The Formula XI compounds wherein —NRR, $R_3$ and $R_4$ are as defined above, may be prepared from the appropriate Formula VII compounds wherein $R_3$ and $R_4$ are as defined above and X is an ester that contains a group that is easily displaced (e.g., alkoxy) by condensation with the appropriate formamide acetal.

Typically the Formula VII compound is heated with the formamide acetal at a temperature of 50° C. to 150° C. in an aprotic solvent such as an aromatic solvent, a hydrocarbon solvent, or a chlorinated solvent with an acid catalyst such as a mineral acid or a sulfonic acid for 2 to 8 hours.

The Formula VII compounds, wherein $R_3$ and $R_4$ are as defined above and X is an ester that contains a group that is easily displaced (e.g., alkoxy), may be prepared from the appropriate Formula VIII compound and consequentlythe appropriate Formula IX and X compounds in an analogous manner to that described above.

The starting materials/reagents for the above described reaction schemes (e.g., Formula IX and X compounds, the amines, the alkyl oxalates, the alkyl compounds, $R_5C(O)NH_2$, $R_5C(OR)_3$, formamide acetals or amines) can be easily synthesized by those skilled in the art starting from common chemical reagents using conventional methods of organic synthesis. In addition, the prodrugs claimed herein can be easily synthesized by those skilled in the art using standard methods of organic synthesis and in light of the information contained herein. Some of the preparation methods described herein may require protection of remote functionality. The need for these protecting groups will vary depending on the nature of the remote functionality and the conditions of the preparation methods. This need is readily determined by one skilled in the art. For a general description of protecting groups (e.g., halo($C_1$–$C_4$)alkyl, ($C_1$–$C_4$) alkoxymethyl, arylmethyl and tri($C_1$–$C_4$)alkylsilyl) and their use, see T. W. Greene, *Protective Groups in Organic Synthesis,* John Wiley & Sons, New York, 1991.

Some of the compounds of this invention are acidic and can form a salt with a pharmaceutically acceptable cation. Some of the compounds of this invention are basic and can form a salt with a pharmaceutically acceptable anion. All such salts are within the scope of this invention and can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

The compounds of this invention are all readily adapted to therapeutic use as tyrosine kinase inhibitors for the treatment of tyrosine kinase dependent diseases in mammals (e.g. humans). Tyrosine kinase dependent diseases refer to hyperproliferative disorders which are initiated/maintained by aberrant tyrosine kinase enzyme activity. Examples of such diseases are cancer, atherosclerosis, antiangiogenesis (e.g., tumor growth, diabetic retinopathy), etc. Exemplary types of cancer include breast, colon and uterine cancer.

The in vitro tyrosine kinase inhibitory activity of the compounds of this invention may be demonstrated by methods based on standard procedures. In one method the enzyme pp60src, a tyrosine-specific phosphokinase (tyrosine kinase) associated with the inner surface of the plasma membrane, is purified from Rous sarcoma virus-transformed rat cells. In the basic assay the enzyme is incubated with the substrate, va15 angiotensin II, and gamma-32p-ATP in a total volume of 25 µl for 25 minutes at 30° C. according to Wong, T. W., Goldberg, A. R. *J. Biol. Chem.,* 259, 8505–8512 (1984). The reaction is terminated by the addition of 45 µl of 5% TCA, incubated on ice for 5 minutes and centrifuged for 1 minute to remove precipitated protein. 35 µl aliquots of the supernatants are applied to phosphocellulose paper circles, which are then washed in 3 changes of 0.5% $H_3PO_4$, acetone-rinsed, dried and counted by liquid scintillation. For screening, the compound to be tested is included in the 25 µl incubation mixture; compounds are tested at $10^{-4}$ M, $10^{-5}$ M and $10^{-6}$ M and appropriate solvent controls are included in all assays.

The compounds of this invention are administered either orally or parenterally, or topically (e.g., eye drops), in dosages ranging from about 0.1 to 10 mg/kg of body weight per day in single or divided doses. In any event the amount and timing of compound(s) administered will, of course, be dependent on the subject being treated, on the severity of the affliction, on the manner of administration and on the judgment of the prescribing physician. In particular situations, at the discretion of the attending physician, doses outside of this range will be used.

Methods of preparing various pharmaceutical compositions with a certain amount of active ingredient are known, or will be apparent in light of this disclosure, to those skilled in this art. For examples, see *Remington's Pharmaceutical Sciences,* Mack Publishing Company, Easter, Pa., 15th Edition (1975).

The compounds of this invention can be administered in a wide variety of different dosage forms, i.e., they may be combined with various pharmaceutically-acceptable inert carriers in the form of tablets, capsules, lozenges, troches, hard candies, powders, sprays, elixirs, syrups, injectable or eye drop solutions, and the like. Such carriers include solid diluents or fillers, sterile aqueous media and various non-toxic organic solvents.

For purposes of oral administration, tablets containing various excipients such as sodium citrate, calcium carbonate and calcium phosphate are employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the essential active ingredient therein can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble, alkali metal or alkaline-earth metal salts previously enumerated. Such aqueous solutions should be suitably buffered, if necessary, and the liquid diluent first rendered isotonic with sufficient saline or glucose. These particular aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of topical administration, dilute sterile, aqueous solutions (usually in about 0.1% to 5% concentration), otherwise similar to the above parenteral solutions, are prepared.

In a pharmaceutical composition comprising a compound of this invention, or a pharmaceutically-acceptable salt or prodrug thereof, the weight ratio of carrier to active ingredient will normally be in the range from 1:4 to 4:1, and preferably 1:2 to 2:1. However, in any given case, the ratio chosen will depend on such factors as the solubility of the active component, the dosage contemplated and the precise route of administration.

EXAMPLES 1–12

The following 5,10-dihydropyrimido[4,5-b]quinolin4(1 H)-ones were prepared from the corresponding pyrimido[4,5-b]quinolin-4(1 H)-ones using an analogous procedure to that described in: Campaigne, E.; Randau, G. *J. Het. Chem.,* 1971, Vol. 8, p. 111.

EXAMPLE 1

5,10-Dihydro-7-methoxypyrimido[4,5-b]quinolin-4(1 H)-one; m.p.>300° C.(DMF). Anal. Calc'd for $C_{12}H_{11}N_3O_2$: C, 62.87; H, 4.84; N, 18.33. Found: C, 62.79; H, 4.67; N, 18.30.

EXAMPLE 2

5,10-Dihydro-8-methoxypyrimido[4,5-b] quinolin-4(1 H)-one; m.p.>300° C.(DMF). Anal. Calc'd for $C_{12}H_{11}N_3O_2$: C, 62.87; H, 4.84; N, 18.33. Found: C, 62.69; H, 4.65; N, 18.25.

EXAMPLE 3

5,10-Dihydro-7,8-dimethoxypyrimido [4,5-b]quinolin-4(1 H)-one; m.p. 303° C. dec (DMF).

EXAMPLE 4

5,10-Dihydro-2-ethylpyrimido[4,5-b]quinolin-4(1 H)-one; m.p. 281–283° C. dec (AcOH/$H_2O$).

EXAMPLE 5

5,10-Dihydro-7,8-dimethoxypyrimido[4,5-b]quinolin-4(1 H)-one-2-(N-((3'-morpholino)propyl)carboxamide); m.p. 239–243° C. Anal. Calc'd for $C_{21}H_{27}N_5O_5.H_2O$: C, 56.62; H, 6.56; N, 15.72. Found: C, 56.40; H, 6.23; N, 15.87.

EXAMPLE 6

5,10-Dihydro-7,8-dimethoxy-3-(3'-((N-morpholino))propyl)pyrimido[4,5-b]quinolin-4(1 H)-one; m.p. 178–180° C. (EtOH/acetone/hexanes). Anal. Calc'd for $C_{20}H_{26}N_4O_4.0.5 H_2O$: C, 60.74; H, 6.88; N, 14.17. Found: C, 60.42; H, 6.59; N, 14.00.

EXAMPLE 7

5,10-Dihydro-7-thio(4-methoxyphenoxy)pyrimido[4,5-b]quinolin4(1 H)-one;m.p. 280–283° C. Anal. Calc'd for $C_{18}H_5N_3O_2S.0.5 H_2O$: C, 62.42; H, 4.66; N, 12.13. Found: C, 62.79; H, 4.27; N, 12.50.

EXAMPLE 8

5,10-Dihydro-8-ethoxy-7-methoxypyrimido[4,5-b]quinolin-4(1 H)-one; m.p. 318–320° C. Anal. Calc'd for $C_{14}H_{15}N_3O_3.0.25 H_2O$: C, 60.54; H, 5.63; N, 15.13. Found: C, 60.57; H, 5.27; N, 15.15.

EXAMPLE 9

5,10-Dihydro-7-ethoxy-8-methoxypyrimido[4,5-b]quinolin-4(1 H)-one; m.p. 335–336° C. Anal. Calc'd for $C_{14}H_{15}N_3O_3.0.12 H_2O$: C, 61.03; H, 5.58; N, 15.26. Found: C, 60.99; H, 5.27; N, 15.31.

EXAMPLE 10

5,10-Dihydro-8-butoxy-7-ethoxypyrimido[4,5-b]quinolin-4(1 H)-one; m.p. 324–325° C. Anal. Calc'd for $C_{17}H_{21}N_3O_3.0.5 H_2O$: C, 62.95; H, 6.84; N, 12.90. Found: C, 62.85; H, 6.45; N, 12.90.

EXAMPLE 11

5,1-Dihydro-8,9-dimethoxypyrimido [4,5-b]quinolin-4-(1 H)-one; m.p. 261–263° C. Anal. Calc'd for $C_{13}H_{13}N_3O_3.0.12 H_2O$: C, 59.71; H, 5.11; N, 16.07. Found: C, 59.72; H, 4.87; N, 16.26.

EXAMPLE 12

5,10-Dihydro-6,9-dimethoxypyrimido[4,5-b]quinolin-4(1 H)-one; m.p.>300° C. (DMF/$H_2O$). Anal. Calc'd for $C_{13}H_{13}N_3O_3$: C, 60.22; H, 5.05; N, 16.21. Found: C, 60.04; H, 4.95; N, 16.23.

EXAMPLE 13

5,10-Dihydro-7,8-dimethoxy-3-methylpyrimido [4,5-b]quinolin-4(1 H)-one

To a heated (90° C.), stirred solution of 7,8-dimethoxy4-oxo-3,4,5,10-tetrahydropyrimido[4,5-b]quinoline (0.25 g, 0.96 mmol) and sodium hydroxide (0.05 g, 1.25 mmol) in water (3 mL) was added dimethylsulfate (0.23 mL, 2.4 mmol). After 0.5 hour, the reaction mixture was diluted with water (20 mL), the solids filtered, washed with acetonitrile and dried in vacuo to afford 0.13 g of the title compound; m.p. 225–230° C.

FORMULA VII INTERMEDIATES

The following 2-aminoquinoline-3-carboxamide/carboxylateesters were prepared according to analogous procedures to that described in: Campaigne, E.; Randau, G. *J. Het. Chem.* 1971, Vol. 8, p. 111.

PREPARATION A

2-Amino-6-methoxyquinoline-3-carboxamide; m.p. 232–233° C.

PREPARATION B

Ethyl 2-Amino-7-methoxyquinoline-3-carboxylate; m.p. 151–154° C.

PREPARATION C

2-Amino-6,7-dimethoxyquinoline-3-carboxamide; m.p. 275° C. (pyridine).

PREPARATION D

Ethyl 2-Amino-6,7-dimethoxyquinoline-3-carboxylate; m.p. 188–189.5° C.

PREPARATION E

2-Amino-7,8-dimethoxyquinoline-3-carboxamide; m.p. 218–219° C.

PREPARATION F

2-Amino-6-thio(4-methoxyphenoxy)-3-carboxamide; m.p. 236–239° C.

PREPARATION G

2-Amino-7-butoxy-6-ethoxy-3-carboxamide; m.p. 225° C.

PREPARATION H

2-Amino-6-ethoxy-7-methoxy-3-carboxamide; m.p. 263–264° C.

PREPARATION I

2-Amino-7-ethoxy-6-methoxy-3-carboxamide; m.p. 234–235° C.

PREPARATION J

2-Amino-5,8-dimethoxy-3-carboxamide; m.p. 263–264° C.

FORMULA XIV INTERMEDIATES

The following pyrimido[4,5-b]quinolin-4(1 H)-ones were prepared from the corresponding 2-amino-quinoline-3-carboxamides/carboxylate esters according to an analogous procedure to that described in: Campaigne, E.; Randau, G. *J. Het. Chem.* 1971, Vol. 8, p. 111.

PREPARATION K

7-Methoxypyrimido[4,5-b]quinolin-4(1 H)-one; m.p.>300° C. (DMF). Anal. Calc'd for $C_{12}H_9N_3O_2$: C, 63.43; H, 3.99; N, 18.49. Found: C, 63.09; H, 3.71; N, 18.43.

PREPARATION L 7,8-Dimethoxypyrimido[4,5-b]quinolin-4(1 H)-one; m.p. 311–312° C. (AcOH).

PREPARATION M

7-Ethoxy-6-methoxypyrimido[4,5-b]quinolin-4(1 H)-one; m.p. 330–331° C. Anal. Calc'd for $C_{14}H_{13}N_3O_3O_3 \cdot 1.8 H_2O$; C, 61.48; H, 4.88; N, 15.37. Found: C, 61.58; H, 4.61; N, 15.30.

PREPARATION N

6-Ethoxy-7-methoxypyrimido[4,5-b]quinolin-4(1 H)-one; m.p. 348–349° C. Anal. Calc'd for $C_{14}H_{13}N_3O_3 \cdot 1.8 H_2O$: C, 61.48; H, 4.88; N, 15.37. Found: C, 61.48; H, 4.65; N, 15.48.

PREPARATION 0

7-Butoxy-6-ethoxypyrimido[4,5-b]quinolin-4(1 H)-one; m.p. 280° C. (dec).

FORMULA XIV INTERMEDIATES

2-Ethylpyrimido[4,5-b]quinolin-4(1 H)-one

A slurry of 2-aminoquinoline-3-carboxamide (1.0 g, 5.3 mmol), (Campaigne, E.; Randau, G. *J. Het. Chem.* 1971, Vol. 8, p. 111) and p-toluenesulfonic acid-monohydrate (50 mg) in triethyl orthopropionate (25 mL) was refluxed for 24 hours. After cooling, the reaction mixture was diluted into diethyl ether (50 mL), the resulting solids filtered and washed with diethyl ether. The solids were recrystallized from formamide to afford 0.14 g of the title compound; m.p. 240–245° C.

FORMULA XIV INTERMEDIATES

Ethyl 7,8-dimethoxypyrimido[4,5-b]quinolin-4(1 H)-one-2-carboxylate

A slurry of 2-amino-6,7-dimethoxyquinoline-3-carboxamide (1.0 g, 4.2 mmol) in diethyloxylate (25 mL) was heated at 205° C. for 3 hours. After cooling, the solids were filtered, dissolved in warm chloroform (100 mL), treated with charcoal and filtered. The filtrate was concentrated in vacuo to afford 0.40 g of the title compound; m.p. 268–269° C.

FORMULA IV INTERMEDIATES 7,8-Dimethoxvpyrimido[4,5-b]quinolin-4(1 H)-one-2-(N-((3'(N-morpholino)propvl)carboxamide)

A stirred slurry of ethyl 7,8-dimethoxypyrimido[4,5-b]quinolin-4(1 H)-one-2-carboxylate (1.0 g, 3.0 mmol) and 4-(3-aminopropylmorpholine (0.9 g, 6.0 mmol) in dimethylformamide was refluxed for 2 hours. The reaction mixture was allowed to cool and then diluted into ice water. The resulting solids were filtered, washed With acetonitrile and dried in vacuo to afford 0.8 g of the title compound; m.p. 227–229° C.

FORMULA Xl INTERMEDIATES

Ethyl 2-((dimethylamino)methylimino)-6,7-dimethoxyguinoline-3-carboxylate

A solution of ethyl 2-amino-6,7-dimethoxyquinoline-3-carboxylate (0.5 g, 1.8 mmol), 1,1-dimethoxytrimethylamine (0.5 g, 4.5 mmol) and p-toluenesulfonic acid in toluene (10 mL) was refluxed for 4 hours. The reaction mixture was concentrated in vacuo, dissolved in hot benzene, treated with charcoal, filtered and the filtrate concentrated in vacuo. The solids were recrystallized from hexane to afford 0.4 g of the title compound; m.p. 125–128° C.

FORMULA V INTERMEDIATES 7,8-Dimethoxy-3-(3'-((N-morpholino))propyl)pyrimido[4,5-b]quinolin-4(1H)-one A solution of ethyl 2-((dimethylamino)methylimino)-6,7-dimethoxyquinoline-3-carboxylate (1.0 g, 3.0 mmol) and 4-(3-aminopropylmorpholine (0.9 g, 6.0 mmol) in ethanol (15 mL) was refluxed for 4 hours, the reaction mixture allowed to cool and the resulting solids filtered. Recrystallization afforded 1.0 g of the title compound as a yellow solid; m.p. 258.5–259° C.

It should be understood that the invention is not limited to the particular embodiments described herein, but that various changes and modifications may be made without departing from the spirit and scope of this novel concept as defined by the following claims.

I claim:

1. A compound of Formula I

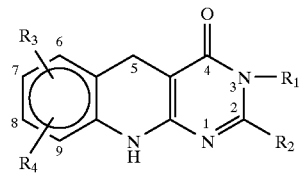

Formula I or their pharmaceutically acceptable salts thereof wherein $R_1$ is H, alkyl($C_1$–$C_4$) or morpholinoalkyl ($C_1$–$C_4$);

$R_2$ is morpholinoalkyl($C_1$–$C_4$)carbamoyl, or alkyl ($C_1$–$C_4$); and $R_3$ and $R_4$ are each independently H, methoxyphenylthio, or alkoxy($C_1$–$C_6$);

with the proviso that $R_1$, $R_2$, $R_3$ and $R_4$ are not all H.

2. A compound as recited in claim 1 wherein $R_1$ is H, methyl or morpholinopropyl;

$R_2$ is H or morpholinopropylcarbamoyl;

$R_3$ is 7-methoxy; and $R_4$ is 8-methoxy.

3. A compound as recited in claim 1 wherein $R_1$ is H;

$R_2$ is alkyl($C_1$–$C_4$);

$R_3$ is H or 7-methoxy; and $R_4$ is H or 8-methoxy.

4. A compound as recited in claim 1 wherein $R_1$ and $R_2$ are H; and $R_3$ and $R_4$ are each independently alkoxy($C_1$–$C_4$).

5. A compound as recited in claim 4 wherein $R_3$ is 7-alkoxy($C_1$–$C_4$) and $R_4$ is 8-alkoxy($C_1$–$C_4$).

6. A compound as recited in claim 4 wherein $R_3$ and $R_4$ are each independently methoxy.

7. A compound as recited in claim 6 wherein $R_3$ is 6-methoxy or 8-methoxy and $R_4$ is 9-methoxy.

8. A compound as recited in claim 1 wherein $R_1$ and $R_2$ are H; and $R_4$ is 7-methoxy or 8-methoxy.

9. The compound as recited in claim 1 wherein $R_1$, $R_2$ and $R_3$ are H; and $R_4$ is 7-((4-methoxyphenyl)thio).

* * * * *